United States Patent [19]

Rizkalla

[11] Patent Number: 4,625,060
[45] Date of Patent: Nov. 25, 1986

[54] PREPARATION OF ACETIC ACID

[75] Inventor: Nabil Rizkalla, River Vale, N.J.

[73] Assignee: The Halcon SD Group, Inc., Montvale, N.J.

[21] Appl. No.: 268,029

[22] Filed: May 28, 1981

Related U.S. Application Data

[63] Continuation-in-part of Ser. No. 219,786, Dec. 24, 1980.

[51] Int. Cl.$^4$ .................... C07C 53/08; C07C 51/353; C07C 51/12
[52] U.S. Cl. .................... 562/607; 562/517; 562/519
[58] Field of Search ............... 562/517, 607, 606, 519

[56] References Cited

U.S. PATENT DOCUMENTS

| | | | |
|---|---|---|---|
| 2,650,245 | 8/1953 | Thomas et al. | 562/519 |
| 4,133,963 | 1/1979 | Holmes | 562/519 |
| 4,194,056 | 3/1980 | Antoniades | 562/517 |

FOREIGN PATENT DOCUMENTS 2749955  5/1978  Fed. Rep. of Germany ...... 562/519

OTHER PUBLICATIONS

Bryant, F. J., et al, General Papers–Petrochemicals: presented before the American Chemical Society, Dallas Meeting, Apr. 8–13, 1973.

Primary Examiner—Vivian Garner
Attorney, Agent, or Firm—Harold N. Wells

[57] ABSTRACT

Acetic acid is prepared by heating methyl formate in the presence of carbon monoxide by the use of a molybdenum-nickel or tungsten-nickel co-catalyst in the presence of a promoter comprising an organo-phosphorus compound or an organo-nitrogen compound wherein the phosphorus and nitrogen are trivalent, and in the presence of a halide.

4 Claims, No Drawings

PREPARATION OF ACETIC ACID

REFERENCE TO RELATED APPLICATION

This is a continuation-in-part of co-pending application Ser. No. 219,786 filed Dec. 24, 1980.

This invention relates to the preparation of acetic acid and is more particularly concerned with the production of acetic acid from methyl formate, specifically the catalytic rearrangement of methyl formate into acetic acid.

The conversion of methyl formate into acetic acid is a known reaction. U.S. Pat. No. 2,508,513, for example, shows a liquid-phase process in which methyl formate is heated in the presence of a carbonyl-forming metal catalyst and halogen, the catalyst being defined as one or more of the iron metals, preferably nickel. The use of nickel iodide hexa-hydrate and nickel carbonyl is exemplified. The process is carried out at a high temperature and, although no yields are reported, it is apparent from the reference to by-products that they are relatively low. U.S. Pat. No. 1,697,109 discloses the vapor-phase conversion of methyl formate into acetic acid, using as catalysts substances which are acetates or capable of forming acetates Illustrative catalysts of this nature are compounds of copper, tin, lead, zinc and aluminum. No working examples of the process are given. More recently, catalysts based on Group VIII noble metals have been disclosed for this reaction. Thus U.S. Pat. No. 4,194,056 shows the preparation of acetic acid by heating methyl formate in the presence of a soluble rhodium salt and an iodine-containing promoter. Relatively high yields are reported and this patent states that cobalt iodide, cobalt iodide/triphenyl phosphine, methyl iodide, copper chloride/triphenyl phosphine, ferrous chloride/triphenyl phosphine, tungsten hexacarbonyl, rhenium pentacarbonyl and molybdenum hexacarbonyl are not catalysts for this reaction, rhodium being the only satisfactory catalyst. While rhodium gives good results, it is a very expensive catalyst, as are all Group VIII noble metals. U.S. Pat. No. 3,839,428 uses Group VIII or Group IIb metal catalysts but relatively high temperatures and pressures are employed.

It is accordingly the object of the present invention to provide an improved process for the manufacture of acetic acid by the rearrangement of methyl formate which requires neither high temperatures nor Group VIII noble metals and makes possible the production of acetic acid in high yields in short reaction times.

In accordance with the invention, conversion of methyl formate to acetic acid is carried out by using a molybdenum-nickel or a tungsten-nickel co-catalyst in the presence of a promoter comprising an organo-phosphorus compound or an organo-nitrogen compound wherein the phosphorus and nitrogen are trivalent, and in the presence of a halide, preferably an iodide, a bromide and/or a chloride, especially an iodide, and in the presence of carbon monoxide. The surprising discovery has been made that this co-catalyst in combination with the promoter-halide system of the character indicated makes possible the rearrangement of methyl formate not only at relatively low temperatures and pressures but with rapid, high yield production of acetic acid.

Thus, in accordance with the invention, methyl formate is heated in the presence of carbon monoxide, in the presence of a halide, e.g., a hydrocarbyl halide, especially a lower alkyl halide, such as methyl iodide, and in the presence of the co-catalyst and promoter combination which has been identified above.

Carbon monoxide is removed in the vapor phase and, if desired, recycled. Normally-liquid and relatively-volatile components such as alkyl halide, unreacted methyl formate and any by-products present in the final product mixture can be readily removed and separated from each other as by distillation, for recycling, and the net yield of product is substantially exclusively the desired acetic acid. In the case of liquid-phase reaction, which is preferred, the organic compounds are easily separated from the metal-containing components, as by distillation. The reaction is suitably carried out in a reaction zone to which the carbon monoxide, methyl formate, the halide, the co-catalyst and the promoter are fed.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under superatmospheric pressure but, as previously mentioned, it is a feature of the invention that excessively high pressures, which require special high-pressure equipment, are not necessary. In general, the reaction is effectively carried out by employing a carbon monoxide partial pressure which is preferably at least 15 but less than 2,000 psi, most preferably 15 to 1,000 psi and particularly 30 to 200 psi, although CO partial pressures of 1 to 5,000 or even up to 10,000 psi can also be employed. By establishing the partial pressure of carbon monoxide at the values specified, adequate amounts of this component are always present. The total pressure is, of course, that which will provide the desired carbon monoxide partial pressure and preferably it is that required to maintain the liquid phase and, in this case, the reaction can be advantageously carried out in an autoclave or similar apparatus. At the end of the desired residence time the reaction mixture is separated into its several constituents, as by distillation. Preferably, the reaction product is introduced into a distillation zone which may be a fractional distillation column, or a series of columns, effective to separate the volatile components from the product acid and to separate the product acid from the less volatile catalyst and promoter components of the reaction mixture. The boiling points of the volatile components are sufficiently far apart that their separation by conventional distillation presents no particular problem. Likewise, the higher-boiling organic components can be readily distilled away from the metal catalyst components and any organic promoter which may be in the form of a relatively non-volatile complex. The thus recovered co-catalyst as well as promoter, including the halide component, can then be combined with fresh amounts of methyl acetate and carbon monoxide and reacted to produce additional quantities of acetic acid.

Although not necessary, the process can be carried out in the presence of a solvent or diluent. The presence of a higher-boiling solvent or diluent, preferably the product acid itself, will make it possible to employ more moderate total pressures. Alternatively, the solvent or diluent may be any organic solvent which is inert in the environment of the process such as hydrocarbons, e.g., octane, benzene, toluene, xylene and tetralin, or carboxylic acids. A carboxylic acid, if used should preferably be acetic acid since it is preferred that the solvent employed be one that is indigenous to the system, although other carboxylic acids can also be used. A solvent or diluent, when not the product itself, is suitably selected which has a boiling point sufficiently different from the desired product in the reaction mixture so that it can be readily separated, as will be apparent to persons skilled in the art. Mixtures can be used.

The carbon monoxide is preferably employed in substantially pure form, as available commercially, but inert diluents such as carbon dioxide, nitrogen, methane, and noble gases can be present if desired. The presence of inert diluents does not affect the reaction but their presence makes it necessary to increase the total pressure in order to maintain the desired CO partial pressure. Hydrogen which may be present as an impurity is not objectionable and even may tend to stabilize the catalyst. Indeed, in order to obtain low CO partial pressures the CO fed may be diluted with hydrogen or any inert gas such as those mentioned above.

The co-catalyst components can be employed in any convenient form, viz., in the zero valent state or in any higher valent form. For example, the nickel and the molybdenum or tungsten can be the metals themselves in finely divided form, or a compound, both organic or inorganic, which is effective to introduce the co-catalyst components into the reaction system. Thus, typical compounds include the carbonate, oxide, hydroxide, bromide, iodide, chloride, oxyhalide, hydride, lower alkoxide (methoxide), phenoxide, or Mo, W or Ni carboxylates wherein the carboxylate ion is derived from an alkanoic acid of 1 to 20 carbon atoms such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Included among the catalyst components listed above are complexes of the metal co-catalyst components with organic promoter ligands derived from the organic promoters hereinafter described.

Particularly preferred are the elemental forms, compounds which are halides, especially iodides, and organic salts, e.g., acetates. It will be understood that the foregoing compounds and complexes are merely illustrative of suitable forms of the several co-catalyst components and are not intended to be limiting.

The specified co-catalyst components employed may contain impurities normally associated with the commercially available metal or metal compounds and need not be purified further.

The organo-phosphorus promoter is preferably a phosphine, e.g., of the formula

wherein $R^1$, $R^2$ and $R^3$ may be the same or different, and are alkyl, cycloalkyl, or aryl groups, amide groups, e.g., hexamethyl phosphorus triamide, or halogen atoms, preferably containing 1 to 20 carbon atoms in the case of alkyl and cycloalkyl groups, and 6 to 18 carbon atoms in the case of aryl groups. Typical hydrocarbyl phosphines include trimethylphosphine, tripropylphosphine, tricyclohexylphosphine and triphenylphosphine. Preferably the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexylmethylamine, 2,6-diaminopyridine, 2-quinolinol, N,N-diethyltoluamide, imidazole, pyridine, picolines, and the like.

Although generally the organic promoter is added separately to the catalyst system, it is also possible to add it as a complex with any of the co-catalyst metals, such as bis(triphenylphosphine) nickel dicarbonyl and tetrakis (triphenyl phosphite) nickel. Both free organic promoters and complexes promoters can also be used. When a complex of the organic promoter and the co-catalyst metal is used, free organic promoter can also be added.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is generally influenced by the amount of catalyst. However, essentially any amount of catalyst will facilitate the basic reaction and can be considered a catalytically-effective quantity. Typically, however, each catalyst component is employed in the amount of 1 mol per 10 to 10,000 mols of methyl formate, preferably 1 mol per 100 to 5,000 mols of methyl formate, and most preferably 1 mol per 500 to 1,000 mols of methyl formate.

The ratio of nickel to the second co-catalyst component can vary. Typically, it is one mol of the nickel per 0.01 to 100 mols of the second co-catalyst component, preferably the nickel component is used in the amount of 1 mol per 0.1 to 20 mols, most preferably 1 mol per 1 to 10 mols of the second co-catalyst component.

The quantity of organic promoter can also vary widely but typically it is used in the amount of 1 mol per 0.1 to 10 mols of the co-catalyst components, preferably 1 mol per 0.5 to 5 mols, most preferably 1 mol per 1 to 5 mols of the co-catalyst component.

The amount of iodide component may also vary widely but, in general, it should be present in an amount of at least 10 mols per hundred mols of methyl formate. Typically, there are used 10 to 50 mols of the halide per 100 mols of methyl formate preferably 17 to 35 mols per 100 mols. It will be understood, however, that the halide component does not have to be added to the system as a hydrocarbyl halide but may be supplied as another organic halide, or as the hydrohalide, or other inorganic halide, e.g., a salt, such as the alkali metal or other metal salt, or even as elemental halogen.

As previously mentioned, the catalyst system of this invention comprises an organic promoter component, an iodide component and a molybdenum-nickel or tungsten-nickel co-catalyst component. The catalyst system of this invention permits the production of acetic acid in high yields in short reaction times without the use of Group VIII noble metals and the presence of the molybdenum or tungsten makes possible good results with relatively small amounts of co-catalyst component and reduced quantities of nickel.

A particular embodiment of the catalyst comprising the molybdenum-nickel or tungsten-nickel co-catalyst component, the organic promoter component and the halide component can be represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is a halide source which is hydrogen halide, halogen, an alkyl halide wherein the alkyl group contains 1 to 20 carbon atoms or an alkali metal halide, and Q is an organophosphorus compound or an organo-nitrogen compound wherein the phosphorus and the nitrogen are trivalent. Preferred are the nitrogen and phosphorus compounds previously indicated as being preferably used and in the most preferred form Q is a phosphine of the formula

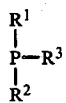

as hereinbefore defined, especially hydrocarbyl phosphines, the molar ratio of X to T being 0.1–10:1, the molar ratio of X+T to Q being 0.05–20:1 and the molar ratio of Z to X+T being 1–1,000:1, preferably 5–100:1. The halide is chloride, bromide or iodide, preferably iodide.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of acetic acid with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most perferably 175° to 255° C., a pressure of 1 to 5,000 p.s.i.a., preferably 50 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention. In the examples, all parts and percentages are by weight, unless otherwise indicated.

EXAMPLE 1

In this example, a magnetically-stirred Hastelloy Parr bomb with a glass liner is employed as the reaction vessel. The bomb is charged with methyl formate (20.5 parts), methyl iodide (40 parts), molybdenum hexacarbonyl (1 part) plus bis-triphenylphosphine nickel dicarbonyl (0.5 part) as co-catalyst and triphenylphosphine (0.5 part) is swept out with argon and is pressured to 700 psig with carbon monoxide. The vessel is heated to 175° C. with stirring. The temperature is maintained at 175° C. After 3 hours reaction, G.C. analysis of the reaction effluent shows it to contain 31.7 wt. % acetic acid. All methyl iodide charged is recovered. This represents a 97% conversion of methyl formate to acetic acid.

EXAMPLE 2

In this example, a magnetically-stirred Hastelloy Parr bomb with a glass liner is employed as the reaction vessel. The bomb is charged with methyl formate (10 parts), methyl iodide (4.4 parts), molybdenum hexacarbonyl (1 part) plus bis-triphenylphosphine nickel dicarbonyl (0.05 part) as co-catalyst, and triphenylphosphine (2 parts), is swept out with argon and is charged with 200 psig H$_2$ and then pressured to 600 psig with carbon monoxide. The vessel is heated to 185° C. with stirring. The temperature is maintained at 185° C. After 5 hours reaction, G.C. analysis of the reaction effluent shows it to contain 42 wt. % acetic acid. This represents a 76% conversion of methyl formate to acetic acid.

EXAMPLE 3

Example 1 is repeated with the exception that bis-triphenylphosphine nickel dicarbonyl is replaced with nickel diiodide. After 3 hours reaction, G.C. analysis of the reaction effluent shows it to contain 32 wt. % acetic acid.

EXAMPLE 4

Example 2 is repeated with the exception that molybdenum hexacarbonyl is replaced with tungsten hexacarbonyl. After 3 hours of reaction, G.C. analysis of the reaction effluent shows it to contain 27 wt. % acetic acid.

EXAMPLE 5

Example 1 is repeated with the exception that the bis-triphenylphosphine nickel dicarbonyl is replaced with nickel tetracarbonyl. After 2½ hours of reaction, G.C. analysis of the reaction effluent shows it to contain no methyl formate. The effluent contains all the charged methyl iodide and 32 wt. % acetic acid.

What is claimed is:

1. A process for the preparation of acetic acid which comprises heating methyl formate with carbon monoxide in the presence of a molybdenum-nickel co-catalyst or a tungsten-nickel co-catalyst, in the presence of a halide and in the presence of a promoter comprising an organo-phosphorus compound or an organo-nitrogen compound wherein the phosphorus and nitrogen are trivalent.

2. A process as defined in claim 1, wherein the co-catalyst is molybdenum-nickel.

3. A process as defined in claim 1, wherein the promoter is a phosphine.

4. A process as defined in claim 3, wherein the co-catalyst is molybdenum-nickel and the promoter is a phosphine.

* * * * *